United States Patent [19]

Baier et al.

[11] Patent Number: 4,670,383

[45] Date of Patent: Jun. 2, 1987

[54] IMMUNE-CHEMICAL MEASUREMENT PROCESS FOR HAPTENS AND PROTEINS

[75] Inventors: Manfred Baier, Seeshaupt; Helmut Jering, Tutzing; Sigmar Klose, Berg, all of Fed. Rep. of Germany

[73] Assignee: Boehringer Mannheim GmbH, Mannheim-Waldhof, Fed. Rep. of Germany

[21] Appl. No.: 775,596

[22] Filed: Sep. 13, 1985

[30] Foreign Application Priority Data

Sep. 13, 1984 [DE] Fed. Rep. of Germany ....... 3433652

[51] Int. Cl.[4] .................. G01N 33/53; G01N 33/543; G01N 33/537; G01N 33/541
[52] U.S. Cl. ......................................... 435/7; 435/28; 435/810; 436/518; 436/536; 436/538; 436/539; 436/540; 436/824; 436/808; 422/61
[58] Field of Search ............................ 435/28, 7, 810; 436/518, 524, 528, 532, 538, 540, 824, 536, 539, 808

[56] References Cited

U.S. PATENT DOCUMENTS 3,720,760 3/1973 Bennich et al. ..................... 436/513
4,048,298 9/1977 Niswender .......................... 436/540

Primary Examiner—Christine M. Nucker
Assistant Examiner—Jack Spiegel
Attorney, Agent, or Firm—Felfe & Lynch

[57] ABSTRACT

This invention describes a process for immuno-chemical quantitative determination of immunologically active substances. The method involves a first incubation of a sample containing the active substance with a labelled binder, which contains an antibody or antibody fragment. After complexing has taken place, solid phase bound active substance identical to the substance being quantitatively determined is added. The solid phase-bound substance binds with free binder, and the solid and liquid phases are separated. A second antibody which is specific either to antibody or the solid phase antibody-substance complex is then added to the liquid phase. This second antibody is non cross-reactive with individual complex components. The amount of labelled first antibody bound to second antibody is then determined.

13 Claims, 3 Drawing Figures

IMMUNE-CHEMICAL MEASUREMENT PROCESS FOR HAPTENS AND PROTEINS

The present invention is concerned with a process for the immunological determination of an antigen-active substance and with a reagent suitable for carrying out this process.

The development of the immune test has, starting from the radio-immuno assay (RIA), resulted in a decisive improvement of the sensitivity and selectivity of the determination of immunogenic substances, such as proteins and haptens, and had achieved great importance, especially in clinical chemical laboratories. Due to the further development of these methods, apart from an increase of labelling methods available, and aside from the field of radioactive labelling, the area of enzyme labelling (EIA) has achieved especial importance. Furthermore development of the reaction techniques have also become considerably differentiated. Thus, tests have been developed which take place not only in homogeneous phase but also in heterogenous phase although, in the case of the latter, the separation of solid and liquid phase, which is usually necessary, can give rise to entrainment and dilution problems.

For such a process, it is particularly desirable to produce a signal which is directly proportional to the amount of the antigen-active substance to be determined, which hereinafter is simply called antigen. Furthermore, a process method is needed in which the disturbance to the technique by components of the solution to be investigated, especially by serum components, can be avoided with certainty. Finally, the process should display a very high sensitivity and even, in the picomole range, at which concentration haptens frequently occur, it should still provide sufficiently accurate results.

It is already known that in the case of the haptens, which give rise to special problems because of their single binding place accessible to antibodies, to carry out the determination it is required that an exactly measured amount of antihapten antibody and of marked hapten are allowed to compete with the hapten to be determined in the sample for the binding to the antibody. (see Federal Republic of Germany Patent Specification No. 21 55 658). In the case of this process, disturbances by foreign components can certainly be excluded but, on the basis of the competitive principle, the sensitivity is too low.

Furthermore, the so-called IEMA process is known in which proteins are determined by reaction with a marked antibody, which is present in any desired excess, and separation of the unreacted antibody with the help of protein present in solid phase, as well as subsequent measurement of the amount of marked antibody remaining in the liquid phase (Lancet, August, 1968, 492–493). Furthermore, from Federal Republic of Germany Patent Specification No. 27 43 444, it is known, in this case of this IEMA process, to use, instead of the complete antibody, Fab fragments thereof and thus to determine haptens and proteins. The disadvantage of this process is that disturbances due to foreign substances are possible and the labelled antibody or its fragment must be precisely measured.

It is object of the present invention to combine the above-mentioned requirements in one process which no longer displays the mentioned disadvantages.

In particular, it is an object of the present invention to remove serum components which are not of interest in the case of the determination or which can interfere, to be able to wash out the solid phase without loss of sensitivity and to achieve an increase of sensitivity.

Thus, according to the present invention, there is provided a process for the immuno-chemical quantitative determination of an antigen-active substance by incubation of the substance to be determined with a binder, which consists of a marked first antibody directed against the substance to be determined or a Fab or Fab' fragment thereof, incubation of the reaction mixture for a definite period of time with the substance to be determined present in solid phase or an analogue thereof, separation of the liquid phase, optional washing of the solid phase and combination of the wash liquid with the liquid phase, wherein the liquid phase is thereafter contacted with a second antibody, present in solid phase, which is directed against the binder or the complex of binder and substance to be determined and cross-reacts with none of the components of the complex when it is directed against the complex, the solid phase is separated off and possibly washed and the label bound thereon is measured.

Surprisingly, the process according to the present invention has a very high degree of precision although two different solid phases are used and, therefore, separation of liquid and solid phase occurs twice. Due to non-specific adsorption on the solid body, it was to have been expected, in the case of such a process, that errors would arise due to entrainment which would exclude the utility of the process. This applies all the more so when additional washing steps after separation of the first solid phase lead to a dilution of the liquid phase.

The process according to the present invention is also especially suitable for the determination of the smallest amounts of haptens, thus of substances which per se are not antigen-active but, by coupling with a further antigen-active substance, can still bring about the formation of specific antibodies. Hitherto, haptens could not be determined by so-called "sandwich" processes since, because of their low molecular weight, they only possess one binding place accessible to antibodies. However, the process according to the present invention is equally suitable for the determination of other antigens and especially of proteins and allergens.

The binder used in the process according to the present invention consists, as already mentioned above, of a labelled first antibody, which is directed against the antigen-active substance to be determined, or a Fab or Fab' fragment thereof. In the scope of the present invention, the binder can be used in any desired excess with regard to the amount of the substance to be determined in the sample. However, it is also possible to use the binder in a molar insufficiency when the period of the incubation with the substance to be determined is chosen to be so short that a non-bound proportion is still present which can react with the substance to be determined present in solid phase. The first antibody can thereby be a polyclonal or a monoclonal antibody.

As labels, one can use those which are conventionally employed in immuno-chemical processes, for example fluorescing or coloured substances, colour development components and the like particularly radio-active atoms and compounds, as well as enzymes. The latter are preferred because of the simplicity with which they can be determined without the use of special apparatus as is needed in the case of radio-active substances, fluorescent markings and the like. As labelling enzymes, these should preferably be used conventionally in enzyme immune assays, such as peroxidase, alkaline phosphatase, β-galactosidase, glucoamylase, glucose oxidase, acetylcholine esterase, catalase, lysozyme, malate dehydrogenase, glucose-6-phosphate dehydrogenase and β-amylase. Peroxidase is especially preferred because of its stability and favourable possibilities of determination by way of the hydrogen peroxide formed, also favourable is galactosidase.

The first solid phase which is used according to the present invention contains bound antigen or an analogue thereof. By analogue there is here to be understood a chemically similar substance which cross-reacts with the first antibody, perhaps though to a lesser extent than the substance itself to be determined. The antigen is preferably bound to an appropriate inert substrate with a covalent or adsorptive bonding or by precipitation. These methods are well known in the art and do not here require further explanation. The same applies to the carrier materials which can be used. As a rule, they are glasses, synthetic resins or synthetic or natural polymers, such as cellulose, dextrans, styrene polymers and the like. Ion exchangers and non-specific adsorbers can also be employed. These carrier materials are also well known in the art. The antigen present in solid phase does not, in the scope of the process according to the present invention, require an exact dosaging. It must only be sufficient to fix, by antigen-antibody reaction, the excess of binder which has not already been bound by the antigen in the sample to be determined.

The second antibody, too, which is also present in insoluble phase, can be present bound to the carrier according to the above-mentioned methods. Here again, in the process according to the present invention, an exact dosaging is not necessary. It suffices when the second antibody is present in an amount sufficient to fix sandwich-like all complex of binder and substance to be determined present in the liquid phase which has not been separated by the substance to be determined present in solid phase. The second antibody can thereby be directed against the first antibody, its Fab or Fab' fragment or against its marking. Alternatively, the second antibody can also be directed against the complex itself which the binder forms with the substance to be determined. In this case, the second antibody must not cross-react either with the marker or with the first antibody in the complex formed, i.e. it must be specific for the bonding between binder and substance to be determined. The second antibody thus binds the antigen-labelled binder complex present in the liquid phase and not bound by the first solid phase and is measured after separation of the liquid phase and washing out of the carrier-bound marking. In the case of enzyme labelling, this takes place simply by contacting with a liquid reagent for the determination of the marking enzyme by methods usual for this purpose. If the label is not an enzyme, then its determination also takes place by means of one of the methods known for this purpose. The second antibody can be polyclonal, monoclonal or a Fab/Fab' fragment thereof.

In the case of the process according to the present invention, depending upon whether binder is added in excess or insufficiency, referred to the substance to be determined, there is obtained, in the case of the first incubation, a reaction mixture which consists of a complex between binder and substance to be determined, residual free binder and possibly residual free substance to be determined. The latter is the case when the incubation is so short that not all of the subtance to be determined enters into the complex and binder is present in an insufficient amount.

By means of the second incubation, on the second phase there is carried out the separation of this reaction mixture since only free binder is fixed on this solid phase but not binder contained in the complex. Therefore, in the case of subsequent phase separation, the complex passes over into the liquid phase and is separated from the latter with the second antibody present in solid phase. Therefore, complex fixed on to the second solid phase contains the labelling of the binder in an amount directly proportional to the substance to be determined. Subsequently, the amount of label is measured. If the label is, for example an enzyme, such as β-galactosidase or peroxidase, then the detection of this enzyme takes place in the manner known for this purpose. The detection of a radio-active label takes place analogously by means of appropriate apparatus and of an optical label by means of optical apparatus.

The process according to the present invention displays a high degree of precision with a variation coefficient which, as a rule, lies between 5 and 10% in the case of the determination of haptens as antigens in a concentration range of about 1 ng./ml.

The process according to the present invention is neither disturbed by other components of the solution to be investigated, which contains the antigen, which especially excludes the frequent disturbances due to serum components, nor does it require an exact dosaging of the various components used, such as binder, antigen present in solid phase and second antibody. Furthermore, the process provides a measurement value which is directly proportional to the amount of antigen to be determined.

The present invention also provides a reagent for the immuno-chemical determination of an antigen-active substance, comprising
(a) a binder which consists of a marked first antibody directed against the substance to be determined or a Fab or Fab' fragment thereof,
(b) antigen present in solid phase
(c) second antibody present in solid phase which is directed against the binder or the complex of binder and substance to be determined and
(d) a system for measurement of the marking substance.

In a preferred embodiment, the reagent according to the present invention contains an enzyme-containing binder, together with a system for the determination of this enzyme.

Figure 1:
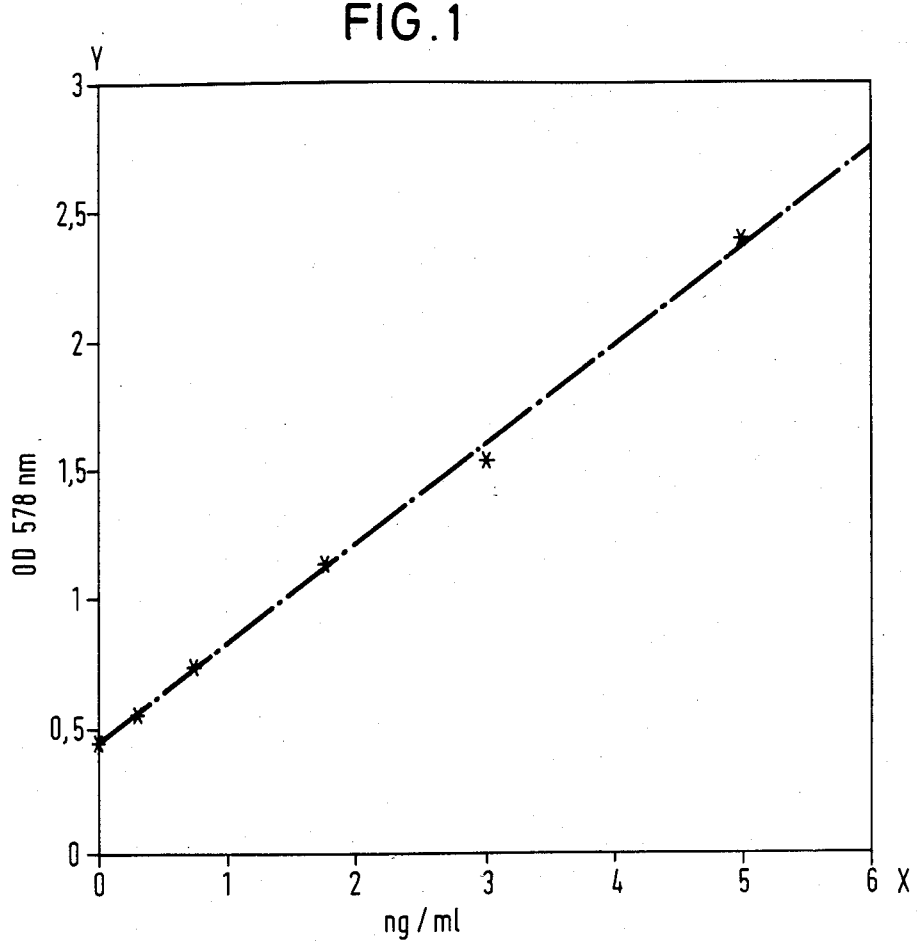
FIG. 1 is a calibration curve of digoxin concentration (X-axis) in undiluted serum plotted against optical density, as elaborated upon in Example 1.

The following Examples are given for the purpose of illustrating the present invention:

EXAMPLE 1

Process for the determination of digoxin in human serum

1. Reagents

Obtaining the antiserum directed against digoxin:

The preparation of the immunogen, namely, human serum albumin conjugated with digoxin, took place in the manner described in detail by V. P. Butler jr. and J. P. Chen, Proc. Nat. Acad. Sci. U.S., 51, 71–78/1967, as well as by T. W. Smith, V. P. Butler and E. E. Haber, Biochemistry, 9, 331–337/1970. Sheep were immunized with this immunogen and the corresponding antiserum obtained.

Obtaining the antiserum against $\beta$-galactosidase:

Sheep were immunized with $\beta$-galactosidase (Boehringer Mannheim GmbH, Order No. 570 079) and the corresponding antiserum obtained (literature: E. Ishiskawa, S. Yoshitake in "Enzyme Immunoassay"; E. Ishikawa, T. Kawai, K. Miyai, eds., Igaku-Shoin, Tokyo/New York, 1981).

Obtaining the antiserum directed against rabbit IgG:

Serum from sacrificed rabbits was mixed with ammonium sulphate to 1.8 M. The precipitate obtained was taken up in a buffer of 15 mM sodium phosphate (pH 7.0) and 60 mM sodium chloride and the solution thus obtained subjected to a passage over DEAE-cellulose. The fractions containing IgG were lyophilized and used as immunogen. Sheep were immunized with this immunogen and the appropriate antiserum was obtained.

Preparation of solid phase 1

Coupling of digoxin to rabbit IgG:

Rabbit IgG was obtained in the above-described manner. Digoxin was oxidized with sodium metaperiodate and coupled to rabbit IgG. The process and the technical details are described in detail by V. P. Butler jr. and J. P. Chen, Proc. Nat. Acad. Sci. U.S., 57, 7/1967, as well as by T. W. Smith et al., Biochem., 9, 331–337/1970. Deviating from these two instructions, rabbit IgG purified over DEAE-cellulose was used as carrier protein instead of serum albumin. Rabbit IgG derivatized with digoxin was coupled to the "affinity adsorbent, glutoraldehyde activated" of Boehringer Mannheim GmbH (Order No. 665 525) according to the manufacturer's working instructions.

Preparation of solid phase 2

The preparation took place by coupling anti-$\beta$-galactosidase IgG fraction to the "affinity adsorbent, glutoraldehyde activated" of Boehringer Mannheim GmbH (Order No. 665 525) according to the manufacturer's instructions. The IgG fractions were obtained from the corresponding antisera via ammonium sulphate precipitation and chromatography over DEAE-cellulose.

Preparation of the binder

Antiserum directed against digoxin was purified via ammonium sulphate precipitation and passage over DEAE-cellulose to give the IgG fraction. Papain fission was carried out according to R. R. Porter, Biochem. J., 73, 119–126/1959. The Fab fragments were separated from the non-digested IgG molecules and from the Fc fragments by means of gel filtration over Sephadex G 100 and ion exchange chromatography over DEAE-cellulose according to the instructions given in the literature (K. Malinowski and W. Manski in "Methods of Enzymology"; J. J. Langone and H. van Vunakis, eds., pub. Academic Press, Vol. 73, 418–459/1981). The resutling Fab fraction was passed over a column provided with solid phase 1. The first elution buffer was 0.1 M sodium phosphate (pH 7.2) plus 0.9 M sodium chloride. After elution of the non-specific Fab fragments, i.e. Fab fragments not directed against digoxin, those Fab fragments directed against digoxin were eluted with 1 M propionic acid. The eluate was subsequently dialysed against water, concentrated by ultrafiltration and lyophilized. The Fab fragments directed against digoxin were reacted with the hetero-bifunctional reagent N-(m-maleic-imidobenzoyloxy)-succinimide (MBS) and subsequently coupled to $\beta$-galactosidase according to the instuctions of T. Kitiwaga in "Enzyme Immunoassay"; Ishikawa, T. Kawai, K. Miyai, eds., Igaku Shoin, Tokyo/New York (1981). After coupling, the Fab-$\beta$-gal conjugate was subjected to a gel filtration over Sepharose 6 B, in the manner described by the mentioned authors. The fractions were used which did not contain any free, i.e. uncoupled, $\beta$-galactosidase.

2. Determination of digoxin

Digoxin standards in human serum (taken from the Elisa kit of Boehringer Mannheim GmbH, Order No. 199 656) were diluted 1:7.5 with a 0.9% aqueous solution of sodium chloride.

To 200 $\mu$l. of diluted standard were added 200 $\mu$l. of binder (20 mU/Ml., determined with o-nitrophenyl-$\beta$-D-galactoside), prepared as described above. The binder is dissolved in the following buffer:

0.1 M sodium phosphate (pH 7.2)
0.2% sodium chloride
2 mM magnesium chloride
1% bovine serum albumin Standard and binder were incubated at 37° C. for precisely 5 minutes, whereafter 50 $\mu$l. of solid phase 1 were added. The mixture was incubated at 37° C. for a further 5 minutes, while shaking. Subsequently, it was centrifuged for 1 minute with an Eppendorf centrifuge 54/4. 300 $\mu$l. of supernatant were taken, 50 $\mu$l. of solid phase 2 were added thereto and the mixture was incubated at 37° C., while shaking. After the expiry of 5 minutes, the batch was centrifuged, the supernatant discarded and the pellet further washed twice with the above-described buffer. The washed pellet was suspended in 0.6 ml. of a 6 mM solution of chlorophenol red $\beta$-galactoside (preparation see Federal Republic of Germany Patent Specification No. 33 45 748), dissolved in 0.1 M sodium phosphate buffer (pH 7.2), 0.9% sodium chloride and 2 mM magnesium chloride, and incubated for 5 minutes at 37° C., while shaking, whereafter it was centrifuged off in the manner described above. 0.5 ml. of the supernatant were taken and the optical density thereof determined at 578 nm. FIG. 1 of the accompanying drawings shows the course of the calibration curve thus obtained in which the digoxin concentration of the undiluted serum (X axis) is plotted against the related optical density (Y axis).

EXAMPLE 2

Process for the determination of digoxin with the help of a monoclonal antibody directed against digoxin

1. Reagents

There were used or prepared the same reagents as in Example 1 with the exception of the preparation of solid phase 2 and of the binder.

Obtaining the antiserum directed against mouse IgG:

Mouse serum was mixed ad 1.8 M with ammonium sulphate. The precipitate was taken up in a buffer of 15 mM sodium phosphate (pH 7.0) and 50 mM sodium chloride and the solution thus obtained was subjected to a passage over DEAE-cullulose. The IgG-containing fractions were lyophilised and used as immunogen. Sheep were immunised with this immunogen and the corresponding antiserum was obtained.

Preparation of solid phase 2

Sheep IgG directed against mouse IgG was coupled to "Affi-Gel 10" (Amicon) according to the manufacturer's working instructions. Coupling conditions: 5 hours at 4° C. in sodium phosphate buffer (pH 7.5), protein concentration 8 mg./ml. and subsequently 3 hours at ambient temperature with the addition of 0.1 M ethanolamine (pH 8.0).

Preparation of the binder

Monoclonal antibodies against digoxin were prepared according to the method of Kohler and Milstein (Eur. J. Immunol., 6, 292/1976). Ascites containing these monoclonal antibodies against digoxin were purified via ammonium sulphate precipitation and passage over DEAE-cellulose to give the IgG fraction. Papain fission was carried out according to R. R. Porter (Biochem. J., 73, 119–126/1959). The Fab fragments were separated from the non-digested IgG molecules and from the Fc fragments by means of gel filtration over Sephadex G 100 and ion exchange chromatography over DEAE-cellulose according to the method of the literature (K. Malinowski and W. Manski in "Methods in Enzymology"; J. J. Langone and H. van Vunakis, eds., pub. Academic Press, Vol. 73, 418–459/1981). The resulting Fab fraction was passed over a column provided with solid phase 1 prepared as above. The first elution buffer was 0.1 M sodium phosphate (pH 7.2) plus 0.9 M sodium chloride. After elution of the non-specific Fab fragments, i.e. those not directed against digoxin, the Fab fragments directed against digoxin were eluted with 1 M propionic acid. The eluate was subsequently dialyzed against water, concentrated by ultrafiltration and lyophilized. The Fab fragments directed against digoxin were reacted with the hetero-bifunctional reagent N-(m-maleic-imidobenzoyloxy)-succinimide (MBS) and subsequently coupled to β-galactosidase according to the instructions of T. Kitiwaga in "Enzyme Immunoassay"; Ishikawa, T. Kawai, K. Miyai, eds., Igaku Shoin, Tokyo/New York, 1981, pp. 81–89). After coupling, the Fab-β-gal conjugate was subjected to a gel filtration over Sepharose 6 B in the manner described by the mentioned authors. The fractions were used which contained no free, i.e. uncoupled, β-galactosidase.

2. Determination of digoxin

Figure 2:
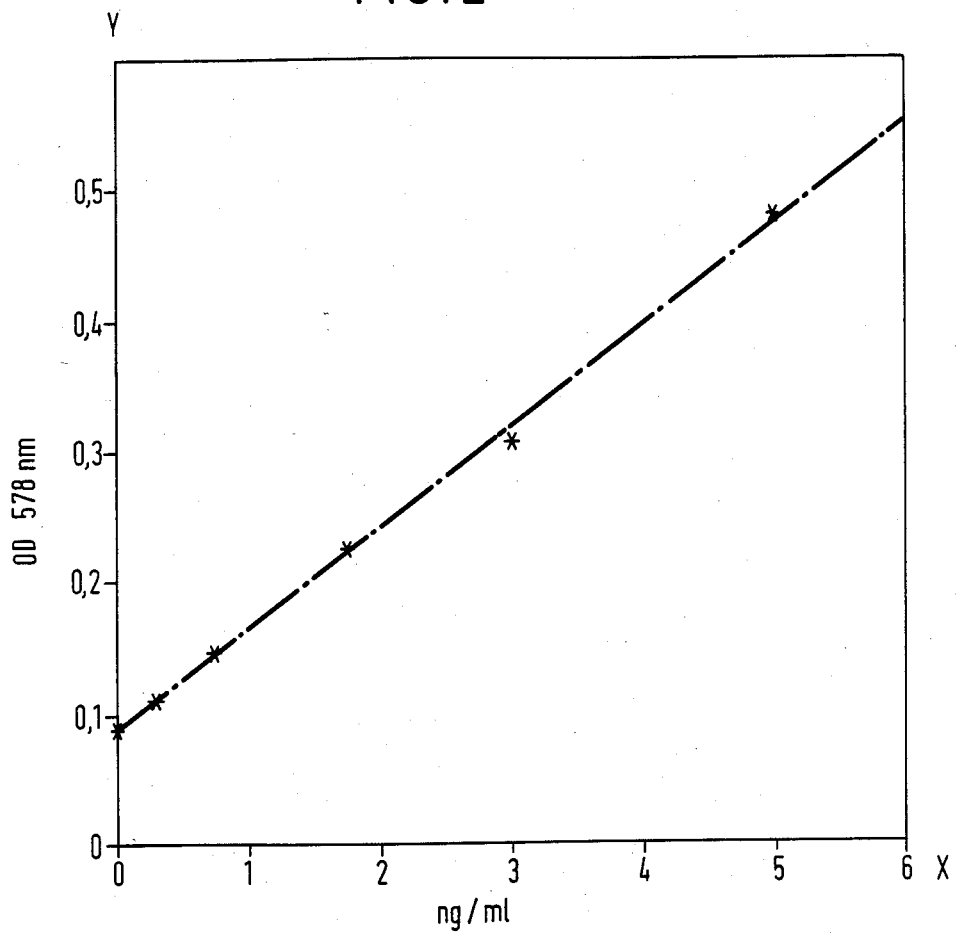
FIG. 2 is a curve similar to FIG. 1, obtained from the data provided by Example 2.

Digoxin standard in human serum (taken from the elisa kit of Boehringer Mannheim GmbH, Order No. 199 656) were diluted 1:7.5 with 0.9% aqueous sodium chloride solution. To 200 μl. of dilute standard were added 200 μl. of binder (20 mU/Ml., determined with o-nitrophenyl-β-D-galactoside), prepared as described above. The binder was dissolved in the following buffer:

0.1 M sodium phosphate (pH 7.2)
0.2% sodium chloride
2 mM magnesium chloride
1% bovine serum albumin Standard and binder were incubated at 37° C. for precisely 5 minutes. Thereafter followed the addition of 50 μl. solid phase 1. The mixture was incubated at 37° C. for a further 5 minutes, with shaking. Subsequently, it was centrifuged for 1 minute with an Eppendorf centrifuge 54/4. 300 μl. of supernatant were taken, 50 μl. of solid phase 2 were added thereto and the batch was incubated at 37° C., while shaking. After 5 minutes, the batch was centrifuged, the supernatant was discarded and the pellet again washed twice with the above-described buffer. The washed pellet was suspended in 0.6 ml. of a 6 mM solution of chlorophenol red β-galactoside, dissolved in 0.1 M sodium phosphate buffer (pH 7.2), 0.9% sodium chloride, 2 mM magnesium chloride, and incubated at 37° C. for 5 minutes, while shaking, whereafter the batch was centrifuged off as above. 0.5 ml. of the supernatant were taken and the optical density thereof determined at 578 nm. FIG. 2 of the accompanying drawings shows the course of the calibration curve produced in this manner in which the digoxin concentration of the undiluted serum (X axis) is plotted against the related optical density (Y axis).

EXAMPLE 3

The determination of digoxin with the use of a digoxin analogue as solid phase 1

1. Reagents

The nature and preparation of the reagents and solid phase 2 correspond to Example 1 with the exception of solid phase 1 and coupling of digoxin to rabbit IgG.

Rabbit IgG was obtained in the above-described manner, oxidised with sodium metaperiodate and coupled to rabbit IgG. The process and the technical details are described in detail by V. P. Butler, jr., and J. P. Chen, Proc. Nat. Acad. Sci, U.S., 57, 7/1967, as well as by T. W. Smith et al., Biochem., 9, 331–337/1970. Deviating from these two instructions, rabbit IgG purified over DEAE-cellulose was used as carrier protein instead of serum albumin.

5 mg. of digitoxin-derivatised rabbit IgG were dissolved in 5 ml. 0.1 M sodium phosphate buffer (pH 7.2) plus 0.9% sodium chloride. To this was added a solution of sheep IgG (see Example 1), directed against rabbit IgG (about 100 mg.), purified via ammonium sulphate fractionation and DEAE-cellulose chromatography, dissolved in the same buffer. A precipitate was formed which was left to stand at ambient temperature for about 1 hour. Thereafter, the precipitate was centrifuged off and subsequently resuspended in 10 ml. of the same buffer. The procedure of centrifuging off and resuspending was repeated 4 times. Subsequently, the precipitate was taken up in 10 ml. of the above-described buffer.

2. Determination of digoxin

Digoxin standards in human serum (taken from the elisa kit of Boehringer Mannheim GmbH, Order No.

Figure 3:
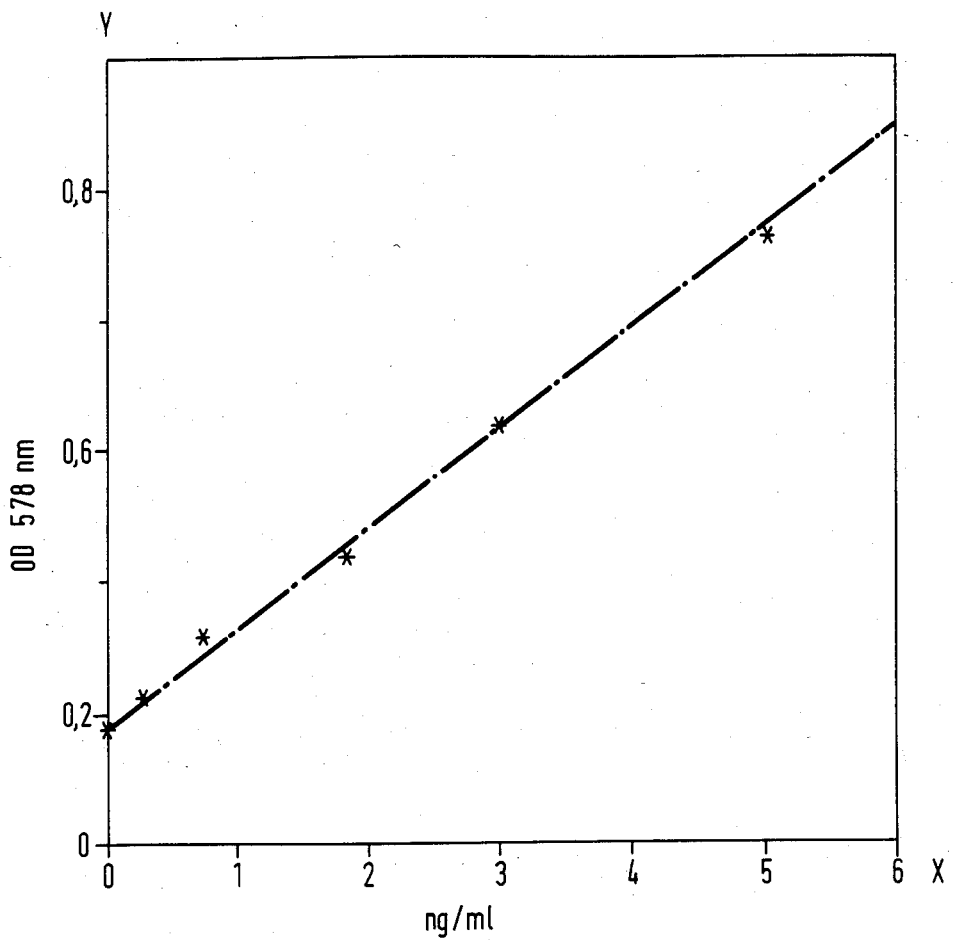
FIG. 3 is also a curve of digoxin concentration against optical density, using the data of Example 3.

199 656) were diluted 1:7.5 with 0.9% aqueous sodium chloride solution. To 200 μl. of diluted standard were added 200 μl. of binder 20 mU/ml., determined with o-nitrophenyl-β-D-galactoside), prepared as described above. The binder was dissolved in the following buffer:
0.1 M sodium phosphate (pH 7.5)
0.2% sodium chloride
2 mM magnesium chloride
1% bovine serum albumin Standard and binder were incubated at 37° C. for precisely 5 minutes, followed by the addition of 50 μl. of solid phase 1. The mixture was incubated at 37° C. for a further 5 minutes, while shaking. Subsequently, it was centrifuged for 1 minute with an Eppendorf centrifuge 54/4. 300 μl. of supernatant were taken and to this are added 50 μl. of solid phase 2, followed by incubation at 37° C., while shaking. After the expiry of 5 minutes, the batch was centrifuged, the supernatant was discarded and the pellet again washed twice with the above-described buffer. The washed pellet was suspended in 0.6 ml. of a 6 mM solution of chlorophenol red β-galactoside, dissolved in 0.1 M sodium phosphate buffer (pH 7.2), 0.9% sodium chloride, 2 mM magnesium chloride, and incubated for 5 minutes at 37° C., while shaking, whereafter it was centrifuged off as above. 0.5 ml. of supernatant were taken and the optical density thereof determined at 578 nm. FIG. 3 of the accompanying drawings shows the course of a calibration curve obtained in this manner in which the digoxin concentration of the undiluted serum (X axis) is plotted against the associated optical density (Y axis).

It will be understood that the specification and examples are illustrative but not limitative of the present invention and that other embodiments within the spirit and scope of the invention will suggest themselves to those skilled in the art.

We claim:

1. A process for the immuno-chemical quantitative determination of an immunologically active substance comprising incubating a sample containing said active substance with a binder, said binder comprising a labelled first antibody specific for said substance or an Fab or Fab' fragment of said antibody under conditions favoring formations of complexes between said substance and said binder, adding solid phase bound active substance identical to the substance to be determined, incubating said solid phase bound active substance and said sample under conditions favoring formation of said solid phase bound active substance and uncomplexed binder separating the solid phase from the sample, contacting said sample with a second antibody in solid phase, said second antibody specifically binding to the binder or the binder-active substance complex, incubating under conditions favoring formation of complexes between said second antibody and said binder or binder-active substance complex, removing said solid phase and measuring the amount of labelled binder bound to said solid phase second antibody.

2. A process as in claim 1, wherein said second antibody is specific for complexes of said binder and active substance but is not cross reactive with the components of said complex.

3. Process of claim 1, wherein said immunologically active substance is a hapten.

4. Process of claim 1, wherein said first antibody is enzymatically labelled.

5. Process of claim 1, wherein said first antibody is enzymatically labelled with a peroxidase.

6. Process of claim 1, wherein said solid phase bound immunologically active substance is bound to said solid phase via covalent, adsorptive, or precipitation bonding.

7. Process according to claim 1, wherein said second antibody is bound via covalent, adsorptive, or precipitation bonding.

8. Process of claim 1 wherein said first antibody is added in an amount exceeding the amount of immunologically active substance in said sample.

9. Process of claim 1, wherein said first antibody is an Fab or Fab' fragment.

10. Process of claim 1, wherein said second-antibody is an Fab or Fab' fragment.

11. A kit useful for immuno-chemical determination of an immunologically active substance comprising separate portions of a binder consisting of a labelled first antibody or a Fab or Fab' fragment thereof which specifically binds to said substance, identical solid phase bound immunologically active substance which complexes to said binder, a second antibody bound to a solid phase, wherein said second antibody specifically binds to said binder, and means for measuring said labelled antibody when bound to said substance.

12. Reagent of claim 11, wherein said first antibody is enzymatically labelled.

13. Reagent of claim 11 wherein said first antibodies is enzymatically labelled with a peroxidase.

* * * * *